United States Patent
Mori et al.

(10) Patent No.: US 6,204,406 B1
(45) Date of Patent: Mar. 20, 2001

(54) CATALYST FOR ASYMMETRIC INDUCTION

(75) Inventors: Atsunori Mori, Tokyo; Yoshitaka Ikeda, Osaka; Koichi Kinoshita, Chiba; Shohei Inoue, Tokyo, all of (JP)

(73) Assignee: Sumitomo Chemical Co., Ltd., Osaka (JP)

(*) Notice: Subject to any disclaimer, the term of this patent is extended or adjusted under 35 U.S.C. 154(b) by 0 days.

(21) Appl. No.: 08/240,811

(22) Filed: May 11, 1994

Related U.S. Application Data

(63) Continuation of application No. 07/595,886, filed on Oct. 1, 1990, now abandoned.

(30) Foreign Application Priority Data

Sep. 29, 1989 (JP) .................................................. 1-256440

(51) Int. Cl.$^7$ ................................................ C07C 253/00
(52) U.S. Cl. ............................................ 558/315; 544/370
(58) Field of Search ........................... 544/370; 514/252; 558/315

(56) References Cited

FOREIGN PATENT DOCUMENTS

| | | |
|---|---|---|
| 0109681 | 5/1984 | (EP) . |
| 0304954 * | 3/1989 | (EP) . |
| 1-53665 | 2/1983 | (JP) . |
| 59-116256 | 7/1984 | (JP) . |
| 59-163344 | 9/1984 | (JP) . |
| 60-42359 | 3/1985 | (JP) . |
| 62-4256 | 1/1987 | (JP) . |
| 62-4257 | 1/1987 | (JP) . |
| 1172383 * | 12/1987 | (JP) . |

OTHER PUBLICATIONS

Mori et al, "Cyclo–((S)–leucyl–(S)–histidyl) . . . Cyanide to Aldehydes", Chemistry Letters, The Chemical Society of Japan, pp. 2119–2122, 1989.

Jun–ichi Oku et al, "Asymmetric Cyanohydrin Synthesis . . . Dipeptide", J.C.S. Chem. Comm., pp. 229–230, 1981.

Yoshiyuki Kobayashi et al, "Asymmetric Addition of Hydrogen . . . Cyclo((S)–phenylalanyl–(S)–histidyl)", Bull, Chem.Soc. Jpn., 59, pp. 893–895, 1986.

F. Schneider, "Reaktivitat cyclisher . . . Fermentkatalyse", Hoppe–Seyler's Z. Phys. Chem., 338, pp. 131–144, 1964.

Aketa et al. Agric. Biol. Chem. 42(4), 895–896, 1978.*

Advances In Pesticide Science Part 2, Pergamon Press Oxford and New York, p. 174–181, 1979.*

* cited by examiner

*Primary Examiner*—Richard L. Raymond
(74) *Attorney, Agent, or Firm*—Sughrue, Mion, Zinn, Macpeak Seas, PLLC

(57) ABSTRACT

(S)-cyanohydrins are produced by asymmetric addition of hydrogen cyanide to aldehydes in the presence of a catalyst of cyclo-[(S)-leucyl-(S)-histidyl].

5 Claims, No Drawings

CATALYST FOR ASYMMETRIC INDUCTION

This is a Continuation of Application Ser. No. 07/595,886 filed Oct. 1, 1990, now abandoned.

This invention relates to a catalyst for asymmetric induction. More particularly, it relates to a catalyst comprising cyclo-[(S)-leucyl-(S)-histidyl] of the formula shown below which is referred to as cyclo-(Leu-His) hereinafter for asymmetric addition of hydrogen cyanide to aldehydes to produce the corresponding (S)-cyanohydrins.

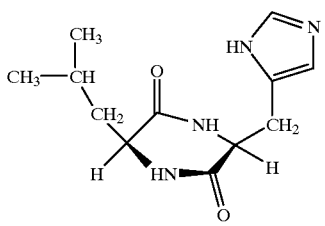

The present inventors reported asymmetric addition of hydrogen cyanide to aldehydes in the presence of a catalyst, i.e., cyclo-[(S)-phenyl-alanyl-(S)-histidyl] [hereinafter described as cyclo-(Phe-His)] to produce the corresponding (R)-cyano-hydrins [Inoue et al, J. Chem. Soc. Chem. Commun., 229 (1981); Bull. Chem. Soc. Jpn., 59, 893 (1986)]. For example, benzaldehyde is allowed to react with hydrogen cyanide in the presence of the cyclo-(Phe-His) to obtain highly pure (R)-mandelonitrile in high yield.

After continued studies on asymmetric induction reactions catalyzed by cyclic peptides, the present inventors found that cyclo-(Leu-His) is useful as a catalyst for asymmetric addition of hydrogen cyanide to aldehydes and that the cyanohydrins obtained thereby are, to their surprise, are in (S)-configuration, while the cyanohydrins obtained by using the cyclo-(Phe-His) as a catalyst are in (R)-configuration. (S)-Cyanohydrins are useful as intermediates for production of (S)-mandelic acid, ferroelectric liquid crystals and insecticides.

The cyclic dipeptide, cyclo-(Leu-His) is a known substance [F. Schneider, Hoppe-Seyler's Z. Phys. Chem. 338, 131 (1964)], which can be prepared according to the usual peptide synthesis. For example, condensation between N-benzyloxycarbonyl-(S)-leucine and methyl ester of (S)-histidine in the presence of isobutyl chloroformate is effected in accordance with the mixed acid anhydride process to obtain methyl ester of N-benzyloxycarbonyl-(S)-leucyl-(S)-histidine and then the ester is hydrogenolyzed in the presence of palladium-carbon, followed by cyclization under reflux in methanol.

Thus obtained cyclo-(Leu-His) is useful as a catalyst for production of (S)-cyanohydrins, for example, (S)-mandelonitrile from benzaldehyde and hydrogen cyanide.

Aldehydes shown below are applicable in such asymmetric cyanation catalyzed by the present catalyst, cyclo-(Leu-His)

aromatic aldehydes such as benzaldehyde, p-methylbenzaldehyde, m-methoxybenzaldehyde, m-phenoxy-benzaldehyde, 4-fluoro-3-phenoxybenzaldehyde, 3-(4-fluorophenoxy) benzaldehyde, 3-(4-chlorophenoxy) benzaldehyde, 3-(4-bromophenoxy)benzaldehyde and 2-thiophenaldehyde aliphatic aldehydes such as 2,2-dimethyl-propanal, 2-methylpropanal, heptanal and undecanal alicyclic aldehydes such as cyclohexane-carboaldehyde.

The asymmetric cyanation is effected usually in the presence of from 1 to 5 mol % of the cyclo-(Leu-His) on the basis of the aldehydes. The reaction is usually carried out by allowing 2 to 5 mol of hydrogen cyanide to react with 1 mol of the aldehydes at a temperature from −20° C. to room temperature in inert solvents such as ethyl ether, isopropyl ether, toluene etc. After the reaction is over, the reaction mixture is, for example, added to dilute hydrochloric acid-methanol solution followed by removal of excess hydrogen cyanide under reduced pressure and the usual work-up to obtain the desired optically active cyanohydrins.

The present invention is explained in further detail in the following examples.

EXAMPLE 1

Synthesis of cyclo-(Leu-His)

To a solution of N-benzyloxycarbonyl-(S)-leucine (5.3 g, 20 mmol) in 40 ml of THF (tetrahydrofuran) were added at −20° C. triethylamine (2.8 ml, 20 mmol) and successively isobutyl chloroformate (2.6 ml, 20 mmol), and the mixture was stirred for 10 minutes.

Separately, to a suspension of methyl ester of (S)-histidine dihydrochloride (5.1 g, 20 mmol) in THF (30 ml) was added triethylamine (5.9 ml, 43 mmol) and the mixture was stirred vigorously for 3 hours. The mixture obtained was added to the aforesaid reaction solution. The mixture was stirred overnight at room temperature with a mechanical stirrer.

After the reaction was over, the reaction mixture was concentrated. To the concentrate were added water and ethyl acetate in order and the mixture was stirred, followed by separation. The organic layer was successively washed with 10% aqueous sodium carbonate solution, aqueous sodium chloride solution and aqueous boric acid solution, and then the solvent was removed. Thus obtained crude acyclic dipeptide was dissolved in methanol (50 ml), and 5% palladium-carbon (0.5 g) was added. The mixture was stirred at room temperature under a hydrogen gas atmosphere to remove the benzyloxylcarbonyl group. After the reaction was over, the palladium-carbon was removed by filtration, and the filtrate was heated under refulx for 3 days in order to carry out a cyclization reaction. The reaction mixture was concentrated to 5 ml and then was dropped into ether (300 ml) to obtain precipitate. The precipitate was collected by filteration and dried in vacuum to obtain 1.6 g of cyclo-(Leu-His).

mp 190–195° C.

IR(KBr) 3250–3650 br, 3100–3250 br, 2960, 1675, 1460, 1340, 840 cm$^{-1}$ $^1$H-NMR (D$_2$O, 270 MHz, δvalue) 7.71(s, 1 H), 6.96(s, 1 H), 4.35–4.42(m, 1 H), 3.90(dd, J=3.9, 9.8 Hz, 1 H), 3.27(dd, J=3.9, 15.1 Hz, 1 H), 3.00(dd, J=4.6, 15.1 Hz), 1.36–1.51(m, 1 H), 1.08–12.1(m, 1 H), 0.75–0.81 (m, 6 H), 0.22–0.37(m, 1 H)

$^{13}$C-NMR (D$_2$O, 67.5 MHz, δvalue) 172.2, 170.2, 137.2, 132.6, 119,9, 56.4, 54.2, 44.6, 32.0, 24.6, 23.8, 21.7
$[\alpha]_D^{25}$ −16.1°(c=1.16, H$_2$O)

EXAMPLE 2

Production of optically active cyanohydrin

To a suspension (0° C.) of cyclo-(Leu-His) (4.8 mg, 0.02 mmol) and benzaldehyde (54 mg, 0.5 mmol) in ether (1 ml) was added at 0° C. hydrogen cyanide (40 μl, 1.0 mmol) by use of a syringe which had been cooled. Stirring was continued for 5 hrs. at 0° C. until almost all of the benzaldehyde was consumed, while being confirmed by TLC.

Then to the reaction mixture was added a dilute hydrochloric acid-methanol solution (250 μl) and the excess hydrogen cyanide was removed under reduced pressure with an alkali trap before a work-up was conducted according to the usual manner. The crude product was purified by silica gel column chromatography to obtain the objective mandelonitrile as a colorless oil. Yield: 85% (calculated by integrated intensity of $^1$H-NMR).

Mandelonitrile obtained was allowed to react with (−)-menthyl chloroformate in the presence of pyridine according to a usual method, [for example, J. W. Westley et al: J. Org. Chem., 33, 3978 (1968)] until the diastereomer of the corresponding menthyl carbonic acid ester was produced. Integrated intensity of the peak signals corresponding to methine proton of cyanohydrin measured by $^1$H-NMR gave 55% ee of optical purity.

In the similar manner as above-mentioned, asymmetric addition reactions to various aldehyde compounds as described below were carried out. That is, 2 equivalent molar amount of hydrogen cyanide was allowed to react in a solvent (1 ml) in the presence of 4 mol % of cyclo-(Leu-His). The results are summarized in the table below.

Cyanohydrins thus obtained were converted into diastereomers of the corresponding menthyl carbonic acid esters (hereinafter referred to as MC ester) or (+)-2-methoxy-2-trifluoromethyl phenyl acetate (hereinafter referred to as MTPA ester) as described above, and the optical purity or optical isomer ratio of the obtained cyanohydrins was measured on the basis of the peak signal intensity corresponding to methine proton of cyanohydrin in $^1$H-NMR analysis or by gas chromatography (GC).

The analysis reveals that cyclo-(Leu-His) induces with priority production of (S)-isomers contrary to the case of cyclo-(Phe-His), since the major peaks of diastereomers when cyclo-(Leu-His) is employed are identical with the minor ones when cyclo-(Phe-His) is employed.

TABLE 1

| Exp. No. | Aldehyde | Solvent | Reaction time (hrs) | Yield a) (%) | Optical purity % ee | Method b) |
|---|---|---|---|---|---|---|
| 1 | Benzaldehyde | Ether | 5 | 85 | 55 | A |
| 2 | " | Isopropyl ether | 6 | 84 | 46 | A |
| 3 | " | Toluene | 6 | 77 | 27 | A |
| 4 | " | Ethyl acetate | 6 | 45 | 19 | A |
| 5 | p-Methylbenzaldehyde | Ether | 5 | 97 | 60 | A |
| 6 | m-Methoxybenzaldehyde | " | 20 | 89 | 56 | A |
| 7 | m-Phenoxybenzaldehyde | " | 24 | 75 c) | 38 | A |
| 8 | 2-Thiophenealdehyde | " | 20 | 66 | 41 | A |
| 9 | 2,2-Dimethylpropanal | " | 5 | 99 | 61 | B |
| 10 | 2-Methylpropanal | " | 5 | 91 | 66 | C |
| 11 | Cyclohexanecarbaldehyde | " | 7 | 83 d) | 64 | C |
| 12 | Heptanal | " | 5 | 98 d) | 74 | C |
| 13 | Undecanal | " | 4 | 93 d) | 81 | C |
| 14 | p-Cyanobenzaldehyde | " | 5 | 96 | 15 | A | a) Unless described otherwise, the yields were calculated by $^1$H-NMR.

b) A: $^1$H-NMR analysis, after converted to MC ester
   B: $^1$H-NMR analysis, after converted to MPTA ester
   C: GC analysis, after converted to MPTA ester c) Reaction at room temperature (no reaction was recognized at 0° C. for 5 hrs.).

d) Calculated after the products were isolated.

What is claimed is:

1. A method for producing (S)-cyanohydrins by allowing hydrogen cyanide to react with aldehydes in the presence of a catalytic amount of cyclo-[(S)-leucyl1-(S)-histidyl].

2. A method for producing (S)-cyanohydrins of aromatic aldehydes by allowing hydrogen cyanide to react with the aromatic aldehydes in the presence of a catalytic amount of cyclo-[(S)-leucyl-(s)-histidyl].

3. The method according to claim 2, wherein said aromatic aldehyde is benzaldehyde which may be substituted with methyl, methoxy, halogen, phenoxy and/or halophenoxy.

4. The method according to claim 2, wherein said aromatic aldehyde is m-phenoxybenzaldehyde which may be substituted with halogen.

5. The method according to claim 1, wherein said aldehydes are aliphatic aldehydes.

* * * * *